United States Patent [19]
Bagby

[11] Patent Number: 5,263,953
[45] Date of Patent: Nov. 23, 1993

[54] APPARATUS AND SYSTEM FOR FUSING BONE JOINTS

[75] Inventor: George W. Bagby, Spokane, Wash.

[73] Assignee: Spine-Tech, Inc., Minneapolis, Minn.

[21] Appl. No.: 815,448

[22] Filed: Dec. 31, 1991

[51] Int. Cl.$^5$ .......................... A61B 17/56; A61F 2/28
[52] U.S. Cl. ......................................... 606/61; 623/16
[58] Field of Search ............... 606/53, 60, 61, 72, 606/73–77; 623/16, 17; 267/162, 166, 168, 289, 290

[56] References Cited

U.S. PATENT DOCUMENTS

| | | | |
|---|---|---|---|
| Re. 31,865 | 4/1985 | Roux | 3/1.912 |
| 14,057 | 2/1916 | Painchaud | 267/179 |
| 1,901,747 | 3/1933 | Holt | 267/179 |
| 1,923,435 | 8/1933 | Gilpin | 267/179 |
| 1,941,882 | 1/1934 | Elder | 267/179 |
| 3,871,031 | 3/1975 | Boutin | 3/1 |
| 4,328,593 | 5/1982 | Sutter et al. | 3/1.91 |
| 4,501,269 | 2/1985 | Bagby | 128/92 |
| 4,549,859 | 10/1985 | Ardrione | 267/179 |
| 4,662,891 | 5/1987 | Noiles | 623/22 |
| 4,743,256 | 5/1988 | Brantigan | 623/17 |
| 4,834,757 | 5/1989 | Brantigan | 623/17 |
| 4,878,915 | 11/1989 | Brantigan | 623/17 |
| 4,961,740 | 10/1990 | Ray | 606/61 |
| 5,015,247 | 5/1991 | Michelson | 606/61 |
| 5,026,373 | 6/1991 | Ray et al. | 606/61 |
| 5,055,104 | 10/1991 | Ray | 606/61 |

FOREIGN PATENT DOCUMENTS 3505567 6/1986 Fed. Rep. of Germany .
2295729 12/1974 France .

OTHER PUBLICATIONS

Otero Vich, Jose M., M.D., "Anterior cervical interbody fusion with threaded cylindrical bone," *J. Neurosurg,* (Nov. 1985), 63:750–753.

*Primary Examiner*—Michael A. Brown
*Attorney, Agent, or Firm*—Wells, St. John, Roberts, Gregory & Matkin

[57] ABSTRACT

A coil fusion implant is formed as a length of wire helically wound up or torqued about a center axis. It has terminal sections at opposed ends that can be releasably gripped and axially twisted about the reference axis to reduce the outer diameter of the coil. The coil can be screwed into place between opposing bony surfaces of a joint while it is constrained in a reduced diameter state. Following its insertion between the prepared bony surfaces, the coil is permitted to gradually recoil as its diameter increases. The coil, in its expanded state then exerts compressive forces radially outward against the bone surfaces in opposition to forces exerted by the ligaments and other tissues connecting the contacted bones of the joint.

8 Claims, 6 Drawing Sheets

APPARATUS AND SYSTEM FOR FUSING BONE JOINTS

TECHNICAL FIELD

This disclosure pertains to surgical fusion of bone joints, such as adjacent spinal vertebrae.

BACKGROUND OF THE INVENTION

Although the immediate effort leading to this disclosure was directed toward the lumbar spine (posterolaterally in approach) the described coil fusion implant for arthrodesis (bone fusion) of two bone parts may be used in any joint having appropriate surrounding soft tissue to provide support when the joint is distracted. The annulus of a lumbar disc is a good example of such tissue.

Basically the principle used in this disclosure is the well known Cloward Technique for the anterior approach in the human cervical region of the spine, in which a solitary dowel of bone is tapped into place in a prepared circular bed slightly smaller than the dowel of bone. It thereby provides its own stability by putting the annulus on stretch and by simple friction.

As a step forward, the Bagby metal dowel (U.S. Pat. No. 4,501,269) utilizes the same principle. That patent discloses a perforated cylindrical hollow implant insertable between prepared surfaces across a joint. Insertion of the implant immediately stabilizes the joint by spreading the bony surfaces apart in opposition to surrounding tissue. Fusion occurs through the implant, which is filled with bone fragments.

The outer surface of the implant described in U.S. Pat. No. 4,501,269 is smooth, but interrupted by numerous openings or fenestrations through which bone ingrowth can occur. One advantage presented by using such an implant made of metal is that any size and shape of implant can be created. It also avoids the disadvantage of having to use bank bone or a separate incision to obtain donor bone from the iliac crest of the patient. The bone morsels harvested in preparing the circular bed are placed into the fenestrated metal cylindrical implant. The implant is then driven or tapped into place in a manner similar to the placement of Cloward's bone dowel.

The rigid metal fusion implant disclosed in U.S. Pat. No. 4,501,269 was an improvement over earlier methods for achieving fusion by use of precut bone dowels. This earlier system, known as "Cloward's Technique" has been expanded to encompass posterior insertion of two dowel bone grafts (Wiltberger's Technique) and the use of threaded surfaces to maintain such grafts in place (Otero-Vich German application No. 3,505,567, published Jun. 5, 1986). Since that date, several U.S. patents have proposed rigid threaded implant structures for placement between adjacent spinal vertebrae.

The present invention arose in an effort to make a transition from use of the anterior cervical approach in horses (where the Bagby Basket has been utilized successfully) to the posterolateral approach in human lumbar spinal areas. Posteriorly-accessed nerve roots can be decompressed (but not anteriorly) as part of the complex surgery. This has necessitated that certain modifications of currently-known fusion systems be carried out.

For safety reasons, a threaded implant offers certain advantages in helping to avoid dislodgement after implantation. Provision of exterior threads about an implant also permits it to be turned into place, in contrast to tapping it axially into place. This offers certain possibilities of better control of the implant during surgery and avoids the possible dangers of the jarring effect of tapping it into place.

Previously described threaded fusion implants attempted to gain the above advantages, but also created a disadvantage in that the provision of threads adds to the outside diameter of the implant. The outer diameter of such fusion implants is critical, since the implant must pass through a limited constriction between the lamina even when the laminae are manually spread.

This added diameter in a fusion implant decreases the remaining volume available within the hollow implant for reception of bone materials in an environment where there is minimal, if any, allowance for such a decrease. The decrease in volume is a function of the square of twice the thread thickness, assuming that the thickness of the wall of the implant is unchanged from that of a non-threaded implant of similar dimensions.

Posterolateral lumbar interbody fusion, in particular, has been slowly gaining popularity in the United States and, to a greater degree, outside the United States. However, posterolateral insertion of implants must be achieved within a relatively small surgical "window" at one or both sides of the vertebral foramen, through which the spinal cord passes. The diameter of the space available for access limits the size of a rigid implant that can be placed between adjacent vertebrae to spread them and immobilize the joint while bone growth occurs.

Because of this constriction it has been conceded that two smaller implants of about 13 mm diameter are required in lumbar fusion applications of such implants. This size limitation contrasts to a single implant of 25 mm diameter that might be used if it were to be inserted anteriorly, where greater accessibility is available. Indeed the bone growth process through such implants requires maximum area of bone contact, which is a function of implant diameter. The size of the vertebral bodies themselves also dictates the need for larger diameter implants. A larger diameter implant seats deeper into cancellous bone, which is more osteogenic. A larger diameter implant also presents greater surface exposure where fusion can occur as a result of bone to implant contact. To further accentuate the problem of implant size due to the restricted window of access plus need to deeply enter the cancellous bone, one needs to realize that the disk thickness of 4 to 6 mm must be overlapped by the implant diameter before it even begins to enter the bone of the vertebrae to be fused.

Two small implants, if well seated, offer better stability than one of the same size; but not necessarily better than that achieved by use of one implant of a significantly larger size. However, the complications involved in placement of two implants inserted from the left and right side in the lumbar region add significantly to the surgery. Furthermore, in preliminary work pertaining to implants in the fetlock joint of horses, it has been reported that after drilling and implanting at one side of a joint, repeating the process at the second side loosened the first implant and in effect voided its intimate contact with the bone surfaces at which fusion was desired. This can currently be avoided only by first drilling both sides and then inserting both implants. However, the process of being incomplete on one side and having to return to it substantially complicates the surgery. If two implants could be inserted from one side or if one implant would suffice in such surgery it would shorten the surgery time and trauma and reduce the resulting scar in the spinal canal by 50%.

This problem of loosening a prior inserted implant is circumvented in the present disclosure by using an implant that is expandable after its implantation.

Threads formed about existing forms of rigid-walled implants can also further separate the viable bone of the vertebrae from the graft bone in the implant cavity of the implant if the thread thickness is added to the existing wall thickness of a non-threaded implant. Such separation is even more exaggerated if the metal threads do not completely seat into viable bone and create void spaces.

The present invention arose from a desire to provide an expandable implant for transverse insertion between bones of a human or animal joint including opposed bony surfaces which are covered and separated by intervening cartilage and surrounded by ligaments which resist expansion of the joint. Specific examples of such joints are a spinal joint between adjacent vertebrae or an ankle joint. The present invention provides an effective, radially-expandable joint capable of securely engaging cancellous bone in a manner that promotes bone ingrowth and prevents the implant from being accidentally dislodged after implantation. It also accommodates variations in the separation between bony surfaces typically encountered when spreading them from one side only due to the limitations imposed by available surgical access.

BRIEF DESCRIPTION OF THE DRAWINGS

Preferred embodiments of the invention are described below with reference to the accompanying drawings, which are briefly described below.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
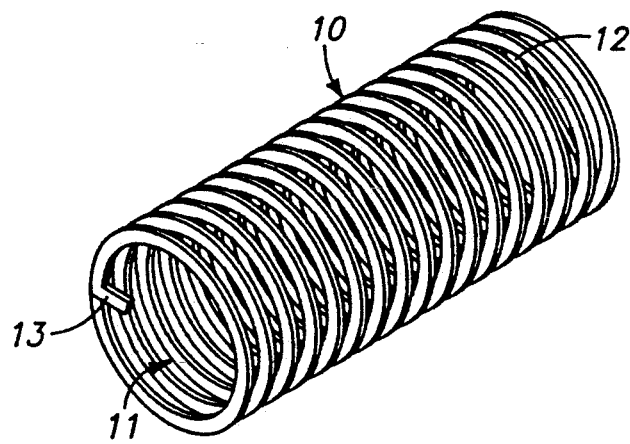
FIG. 1 is a front perspective view of a coil fusion implant.
Figure 2:
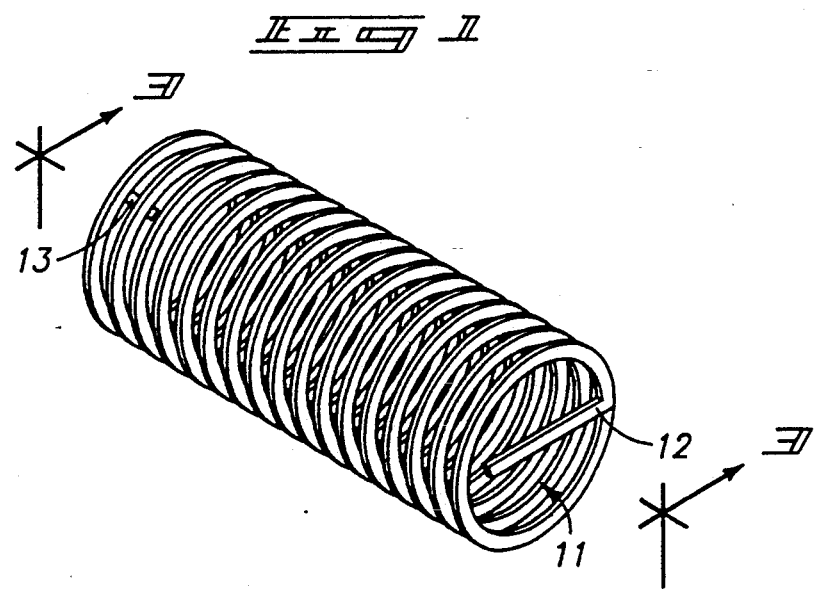
FIG. 2 is rear perspective view.
Figure 3:
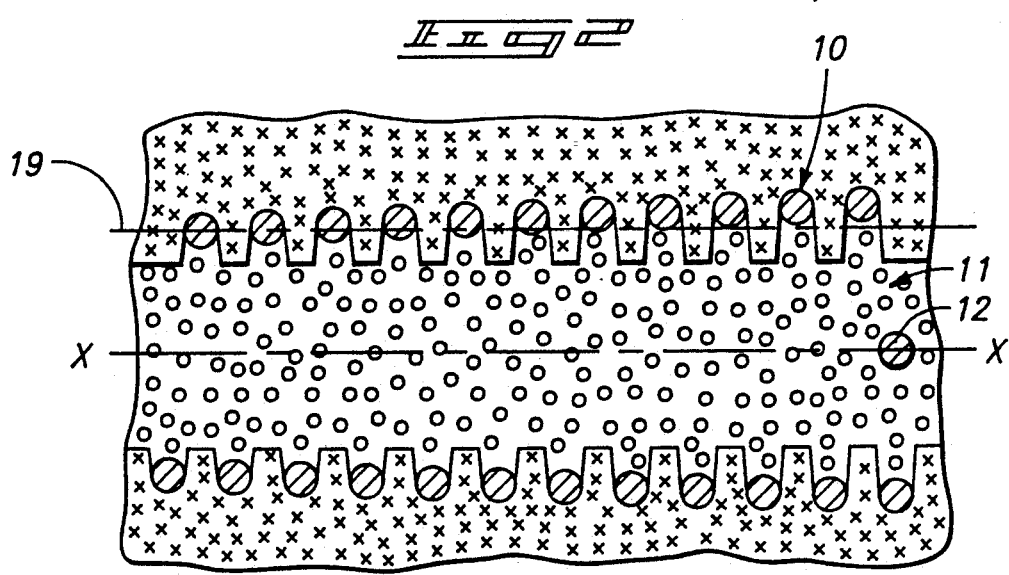
FIG. 3 is an enlarged longitudinal sectional view taken along line 3—3 in FIG. 2.

FIGS. 1-3 illustrate the general structure of a coil fusion implant as contemplated by this disclosure. It comprises a cylindrical helical wire coil 10. The coils 10 are adapted for implantation between prepared bony surfaces of a joint. Implantation might involve placement of one, two, or any multiple of coils 10 as required to stabilize the joint during bone ingrowth through the implanted coil structure.

The distinction between living bone and bone graft materials is graphically presented in the accompanying drawings, which illustrate insertion and implantation of the coil fusion implant. Living bone is shown by surfaces cross-sectioned by a field of crosses (x). Bone fragments and possible other forms of bone graft material used in the fusion method are shown by surfaces cross-sectioned by circles (o). Disk material remaining in the join area is not specifically illustrated, but fills the adjoining spaces outward of the implant location(s).

By way of definition, the coil 10 shall be described with reference to three distinct operational states relative to implantation. The first is the normal "relaxed state" in which it is manufactured. The second is a "torqued state" in which the coil is twisted about its central axis and is mechanically constricted or constrained in a reduced diameter for placement in a joint. The third is the "expanded state" assumed by the freed coil when implanted and restrained between the bones of a joint being fused.

The term "recess" shall refer to the helical spacing between adjacent turns or windings along the illustrated coils 10. The term "implant cavity" shall mean the space bounded by the inner surfaces of each implanted coil 10 and the bony surfaces in contact with it. The implant cavity receives bone fragments and other materials used to induce bone growth through the implanted coil.

The normal diameter of coil 10 while in its relaxed state can be temporarily reduced by holding it in a torqued state in preparation for entry between opposed bony surfaces. This can be accomplished by gripping the first and second terminal sections 12, 13 of the wire that forms coil 10, twisting the coil about its central axis, and maintaining the coil in a twisted condition. The coil diameter can subsequently be permitted to enlarge by twisting the coil in a reverse direction and releasing one or both of the terminal sections 12, 13. This frees the coil 10 to assume its expanded state by recoiling. The diameter of each coil turn or winding will then be determined by its internal spring forces and the external forces exerted upon it by the contacting bony surfaces of the joint being fused. Examples of typical size relationships between the outer diameter of a coil in its three operational states as contemplated by this disclosure are: relaxed state-16.5 mm; torqued state-13 mm; and expanded state-16 mm.

The novelty of this coil fusion implant lies in its ability to radially expand after implantation. Admitting a potentially larger diameter implant through the available restricted surgical window to an implant location provides deeper and wider seating into the cancellous bone.

Each coil 10 is formed as a length of wire wound in repetitive turns centered about a common reference axis (axis X—X in FIG. 3). The wire that forms coil 10 must be constructed of elastic material capable of recoiling to an expanded state of increased outer diameter after being wound up or twisted about its central axis to a torqued state of reduced diameter. The elasticity of the selected wire permits the ends of coil 10 to be twisted relative to one another about the reference axis X—X to an axially torqued state in which its outer diameter is reduced. Coil 10 must also have sufficient compressive strength and elasticity to maintain separation between the bone surfaces of a prepared joint when implanted and permitted to assume a conforming expanded state.

In most instances, the elastic material selected for the wire that forms coil 10 will be a metal alloy suitable for surgical use within the body. However, resin composites and other elastic materials of a permanent nature that are nonreactive when implanted and which have acceptable mechanical strength might be utilized in this application.

The cross-sectional shape of the wire used in coil 10 is not critical to an understanding of the present invention. The shape illustrated in FIG. 3 is circular and commonly used in wire springs for mechanical applications. Other cross-sectional shapes can be substituted, including, but not limited to, ovals, squares, rectangles, diamonds, trapezoids and triangles.

The windings of coil 10 are spaced axially from one another to form a continuous helical recess between them to permit bone ingrowth through the coil fusion implant. No interconnections are attached to the coil that would interfere with projection of prepared bone surfaces radially inward into the enclosure presented by the interior of coil 10. The axial spacing between windings, which form the recesses in the coil 10, can either vary between its three states or can be maintained at a constant value if axial restraining forces are applied to the windings during changes of state.

While the outer diameter of the relaxed coil 10 shown in FIGS. 1 and 2 is constant along its length, it is to be understood that variations in the relaxed state diameter of the windings along coil 10 can be utilized to meet specific surgical applications. As an example, the windings along the inner end of a coil might present a tapered diameter that would facilitate gradual entry between adjacent bone surfaces.

The windings along each coil 10 and the interspersed bony surfaces supporting it within a joint form the boundaries of an open cylindrical implant cavity adapted to receive material promoting bone ingrowth through the coil implant. This implant cavity, designated in FIGS. 1, 2 and 3 by the reference numeral 11, is a perforated space into which bone fragments and other materials that promote bone ingrowth can be placed. As shown in the drawings, it is also advisable to pack bone fragments in the disk space adjacent to the implant to add to the fusion surface. This includes the space axially and radially outward from the implanted coil(s) 10 where disk material has been removed during preparations for implantation.

The wire that forms the coil 10 illustrated in FIGS. 1 and 2 includes first and second terminal sections 12 and 13 at its respective ends. The terminal sections 12, 13 facilitate gripping of the wire by associated tool surfaces, thereby permitting the ends of coil 10 to be axially twisted relative to one another about the axis X—X. Alternative configurations can be provided at the coil terminal sections 12 and 13 to match requirements of insertion tools with which a particular coil is to be used.

Since radial enlargement of coil 10 occurs after implantation, the coil fusion implant can provide an increase in the outer diameter of the coil implant relative to the width of the maximum surgical opening available for access between the opposed bone surfaces of the joint being fused. Such radial enlargement also increases the volume of the implant cavity for the coil implant in comparison to the smaller cavity volume available in rigid implants that must be passed through this restricted space. The increased volume provides a larger amount of bone fragments in the implanted area to promote bone ingrowth through the coil implant.

Expansion of coil 10 after implantation can also fully take up all remaining slack in the surrounding ligaments that resist joint expansion. It has the ability to adapt to variations in pressure and spacing that might be encountered across the implant location. This expansive feature of the coil fusion implant assures that the joint will be immediately stabilized and maintained in an immobile condition to facilitate subsequent bone ingrowth.

The present method for stabilizing a human or animal joint and promoting bone growth across it involves the step of first surgically accessing the joint, using known surgical procedures. This can be accomplished posterolateral, as illustrated, or anterially. Where two or more coil implants are to be used in a joint, they can be placed from either one or both lateral sides of the joint, depending upon accessibility and the surgical procedures utilized.

A retractor (not shown) can be utilized to spread the surfaces of the joint prior to insertion of the coil fusion implant. Preparatory surgery also involves removal of intervening cartilage (disk tissues or other joint material) located between the opposed bony surfaces of the joint in the vicinity immediately adjacent and exterior to the intended placement of the coil implant.

The bony surfaces are next prepared for implantation by cutting cylindrical longitudinal beds into them in configurations complementary to the exterior of the coils 10. The cylindrical bed includes the disk centrally and bone peripherally. These beds are threaded. The female bone threads of the beds later receive the expanded coils of implant 10. The mechanical interlock between the bone threads and the implanted coil serves to insure against accidental dislodgement of coil 10 from the opposed bony surfaces engaged by it.

To prepare a threaded bone bed of approximately 16 mm diameter through a 13 mm window requires a specific sequence of surgical processing:

a) With the spinous process spreader in place the disc is removed and a drill inserted into the disc space cutting a smooth bore bed equally into adjacent vertebrae (approximately 12 mm diameter);

b) A 13 mm threading device is turned into place making superficial threads into the bone. It is temporarily left in place;

c) The spinous process spreader is removed allowing the disc space to narrow and the threading device is turned clockwise and counterclockwise one quarter turns to deepen the threads into the vertebral bodies;

d) A clamp is placed around the two spinous processes to compress and further narrow the disc space and again the threading device is similarly activated. This step helps convert the imperfect cylinder bed (produced by the eccentric spreader) to one having near parallel sides;

e) If more deeply seated threads are needed the tool can be similarly activated while manually adding a vector caudally, cephalad, then left and right laterally;

f) Finally the constrictor is removed, the spreader reinserted and the threading device and bone morsels removed.

A suitably sized coil fusion implant is then selected for placement between the opposed bony surfaces of the joint. The selected coil 10 is next axially twisted to a torqued state where its diameter is temporarily reduced. This can be accomplished by gripping the first and second terminal sections 12, 13 of coil 10 and twisting the coil about its axis. The outer diameter of the coil in its torqued state is less than its outer diameter while in a relaxed state.

Figure 4:
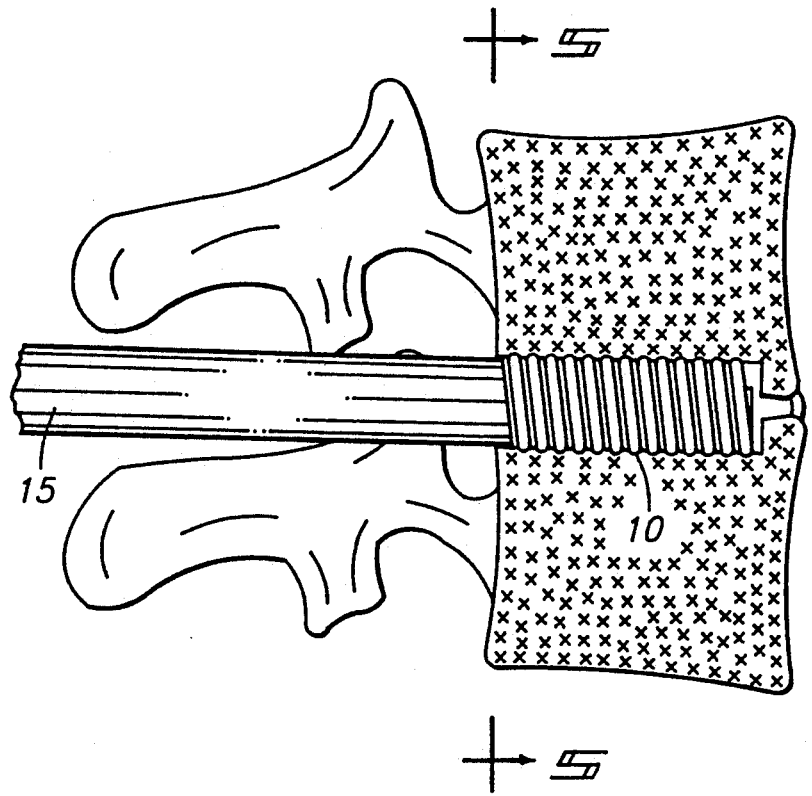
FIG. 4 is a diagrammatic side sectional view illustrating insertion of a coil fusion implant.
Figure 5:
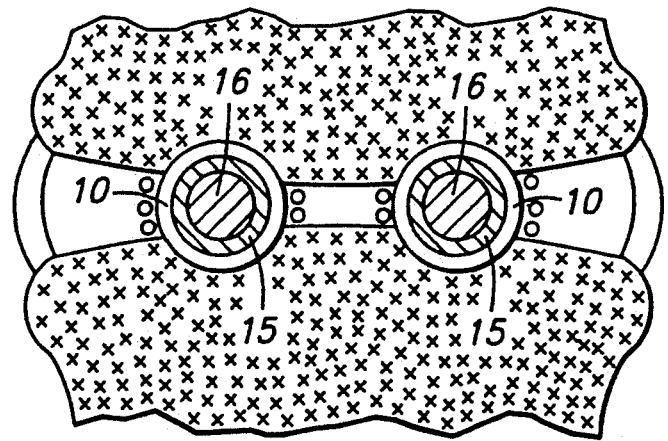
FIG. 5 is a sectional view taken along line 5—5 in FIG. 4.
Figure 6:
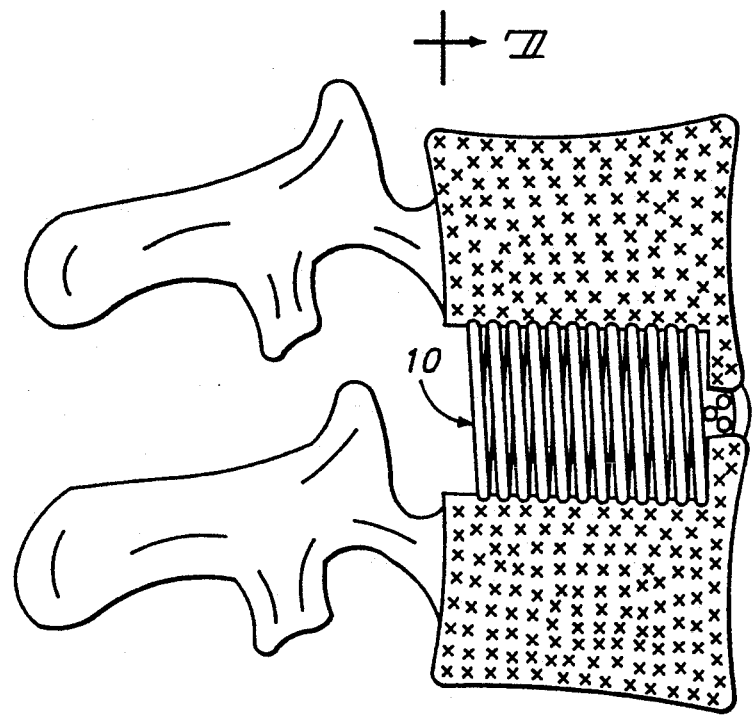
FIG. 6 is a diagrammatic side sectional view showing a fused spinal vertebral joint including a coil fusion implant.
Figure 7:
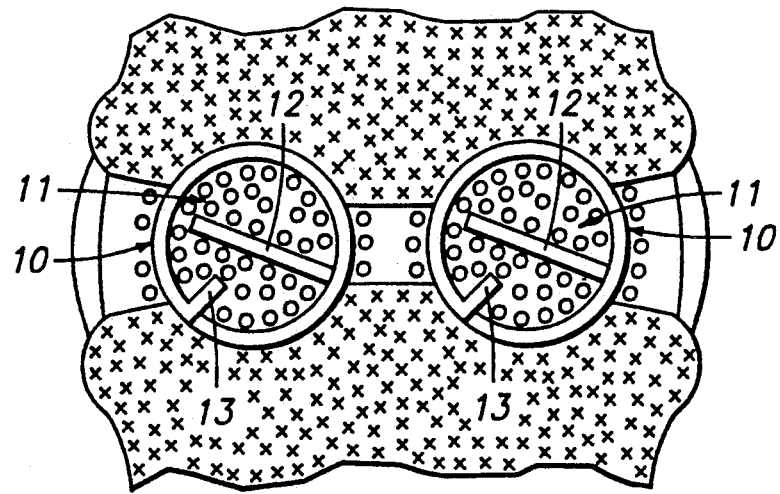
FIG. 7 is a sectional view taken along line 7—7 in FIG. 6.

The wound up coil 10 in its torqued state is next turned into place between the prepared bony surfaces of the joint by use of a suitable insertion tool (see FIGS. 4 and 5). Implantation of the coil 10 is then completed by reverse twisting one or both of its terminal sections 12, 13 and disengaging the insertion tool. This allows coil 10 to gradually recoil and increase in radial size between the constraining bony surfaces of the joint as it assumes its expanded state. The outer diameter of each coil winding will be radially increased to exert a substantially uniform compressive force against the bony surface areas engaged by the coil. The joint will be immediately stabilized by spreading the bony surfaces apart in opposition to the resistance to expansion of the joint provided by the surrounding annulus of ligaments and tissue, reinforced as necessary by a constricting surgical band or suture about the spinous processes.

After implantation a permanent constricting band or figure-of-eight suture is passed around the spinous processes for added fixation. This overcomes the weakness caused by the surgical removal of a portion of the annulus necessary in initially preparing the bed.

While a constant diameter coil 10 will tend to regain its relaxed state diameter following release of its end sections 12, 13, the size of the selected coil 10 should be such that it is to be recognized that constrictions due to forces on the implant will limit its subsequent expansion to a radial size less than that of its relaxed state. Furthermore, the available amount of separation between the bone surfaces might vary from one end of coil 10 to the other. This is particularly true because of the ability of a surgeon to mechanically spread the bones apart only at the face that is accessed. The resulting decrease in spacing inward from this location can be accommodated by the elasticity of the recoiling material in an implanted coil 10, which will assure more even contact and pressure between the windings of the coil and the bone surfaces throughout the length of the coil fusion implant.

In FIG. 3 variations in coil diameter toward the right hand (anterior) end of coil 10 are illustrated with respect to a constant diameter reference line 19. The windings of coil 10 will tend to open wider at locations adjacent positions where the annulus is more relaxed. The end result is constant tautness or pressure on the annulus. Variations in coil diameter will occur to accommodate variations in the annulus expanding to a greater degree where lax and to a lesser degree where already taut.

The implant cavity of each implanted coil 10 is adapted to receive bone fragments and/or other bone growth inducing materials. In most instances, the anterior end of coil 10 will be covered by adjacent tissue or bone. As the surgical site is closed, adjacent tissues will cover the axial end of coil 10 and assist in maintaining the implant cavity within it in a controlled enclosed condition. The posterior end can be further enclosed by a separable cover (not shown) attached to the outermost windings of coil 10 and/or its outer terminal section 13. Such a cover might take the form of a relatively simple circular cap releasably fixed to the coil 10.

Threaded grafts machined from bone have been proposed since as early as 1985 (Otero-Vich German application No. 3,505,567) for use as joint implants for fusion purposes. Such grafts, having machined male threads, can be turned into the implant cavity of a coil 10 to fill or partially fill the coil to promote bone ingrowth through the coil recesses. As in any case involving bone implants, it is vital that there be intimate contact of living bone and the graft material. By combining such threaded grafts and the present coil fusion implant, and filling any remaining void spaces with bone morsels, one can add the strength of the surrounding coil to such grafts. In addition, such an implant will benefit from the immediate rigid fixation of the joint, the deep cutting of the coil windings into cancellous bone, the reduced trauma of surgery, and the ability to collect and use autogenous bone graft material—which all flow from the improved implant characteristics of the coil 10.

Specifically, threaded solid grafts of bone could be turned into an implanted coil 10 following release of an implanting tool or driver. A threaded graft might be in the form of one solid element extending the full axial length of the coil 10 if a piece of suitable bone of such size is available. It might alternatively be in the form of several smaller threaded graft elements arranged coaxially within coil 10 abutting one another to fill its interior. In either case, any remaining void spaces could be filled with small bone fragments to assure intimate contact between living bone and the graft.

It is also practical to use short threaded bone grafts as caps at one or both ends of the implanted coil. One such graft might include a tongue protruding anteriorly to extend beyond the coil 10 and into the disk space for intimate bone-graft contact. A similarly threaded graft, without a tongue, could be used posteriorly to act as a cap and prevent bone materials inside the implant cavity from migration into the spinal canal.

The advantages of using such threaded bone grafts with the present implanted coils are:

they add structural support to the windings of the implanted coil, which are under compression;
they tend to increase the speed of the healing process of the arthrodesis, especially if it is autogenous bone;
they provide intimate contact of loving bone with solid graft, both peripherally and anteriorly;
they offer a cap posteriorly;
they permit use of multiple threaded bone grafts arranged coaxially within the supporting structure of the surrounding coil; and
the use of opposed anterior and posterior caps made from threaded bone grafts can compress free bone fragments or morsels between them to assure intimate bone-graft contact along an implanted coil.

The disclosed surgical system overcomes the disadvantages of devoting critical thickness to creation of threads to axially secure an implant by permitting the threads formed in the receiving bony surfaces to partially extend through the continuous helical recesses that separate the turns of the coil fusion implant (see FIG. 3). Where bone growth materials can be maintained within the coil 10 without capping its ends, the materials within its implant cavity 11 will also allow bone growth in axial directions through the implanted coil to increase the fusion surfaces. This might not be feasible in spinal implantation applications, where new bone formation adjacent to the spinal canal might create too much scar tissue around the dura and nerve roots.

However, attempts should be made to allow some bone graft material to exist posteriorly from the implanted coil 10 by separating the implant from the spinal canal with free fat graft.

The helical nature of coil 10 provides substantial radial recesses for growth of bone through the recesses separating adjacent coil windings. Where the separation between coil turns is equal to their axial thicknesses, the total open area about each area of contact between the coil 10 and the supporting bony surfaces will be 50 percent. So long as adequate compression strength is available in a radial direction across the coil 10, even more space might be provided between the turns. The more open space available, the greater are the opportunities for osteogenesis.

When used between adjacent spinal vertebrae, the implant is preferably inserted posteriorly, but can alternately be inserted anteriorly when such access is indicated. The usual posterolateral lateral access "window" for surgical purposes is approximately 11-13 millimeters in width at both transverse sides of the vertebral foramen. Radial expansion of a coil 10 after implantation increases the available diameter within the implant cavity 11 after implantation, permitting the implant cavity of the coil to hold a greater volume of bone fragments or other bone growth inducing materials in comparison to the volume that can be packed into current hollow threaded implants having a fixed diameter.

As an illustrative example, if the exterior diameter of a rigid unthreaded implant is 13 mm and it is converted to a rigid externally threaded implant of 13 mm outside diameter having 2 mm deep threads, then the implant cavity diameter will be reduced by 4 mm—the total thread depth at its two diametrical sides—to a diameter of 9 mm. This assumes that no change occurs in the implant wall thickness.

Reduction of implant cavity diameter in the coil fusion implant is partially circumvented because the threads are integral with the implant structure. In addition to this advantage the instant implant can be expanded after implantation and increase the implant cavity diameter by approximately 3 mm.

These two factors of salvaging 4 mm and 3 mm are realistic, but not necessarily additive. One cannot expect to gain 7 mm in diameter when comparing the instant coiled implant to a rigid implant with external threads. This is because the diameter of the wire in the coil must be increased beyond normal rigid thread depth for strength and because the total implant cavity volume is differently defined in detail from one implantation to the next. Because of its ability to expand after implantation, an implanted coil 10 (in its expanded state) can be expected to attain an outside diameter of 16-18 millimeters, which makes possible an implant cavity diameter of approximately 11-14 mm.

Since the interior volume of a cylinder is a function of the square of its diameter, even slight increases in the interior diameter of a coil 10, in relation to the inside diameter of alternative fixed-diameter implants, will significantly impact the volume of bone materials that can be utilized within it. An increase in interior diameter of even two millimeters will increase the volume of the implant cavity 11 by a factor of four and an increase of three millimeters will increase the volume of the implant cavity 11 by a factor of nine.

FIGS. 4-8 illustrate implantation of the coils 10 in pairs, the individual coils being inserted from opposite sides of the vertebral foramen. The two coils 10 can either be oriented parallel to one another or can be positioned in an angular relationship. Their orientations across the center of the joint will usually be symmetrical, but can be varied to meet particular surgical requirements. To minimize surgical procedures and complications, two, three, or more coils 10 might also be surgically inserted from a single side of the vertebral foramen. In multiple coil implantations, the individual coils used can have a common diameter in their relaxed states. If desired, coils of differing diameters can be implanted at different surgical locations across the bony joint surfaces.

Figure 8:
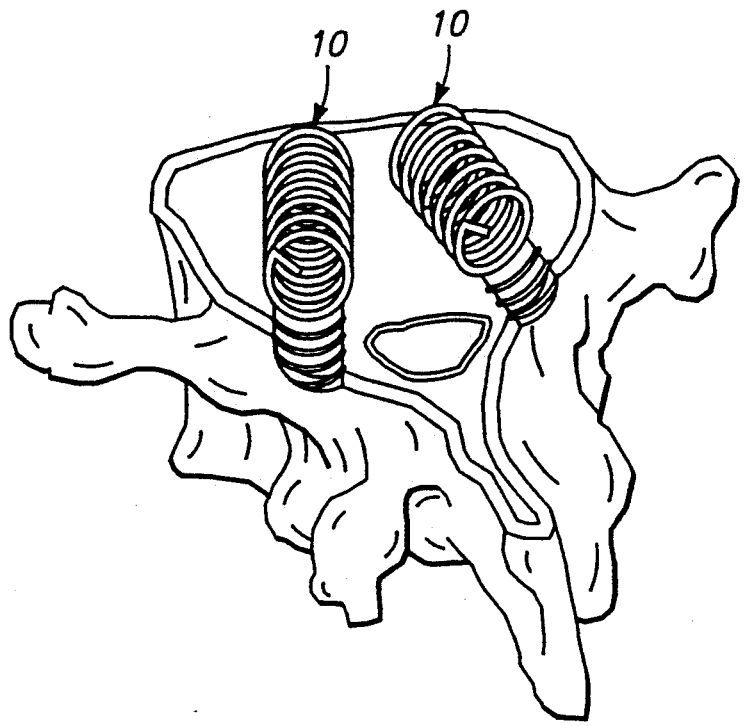
FIG. 8 is a diagrammatic perspective view illustrating two coil fusion implants inserted from opposite sides and positioned on a supporting vertebra.
Figure 9:
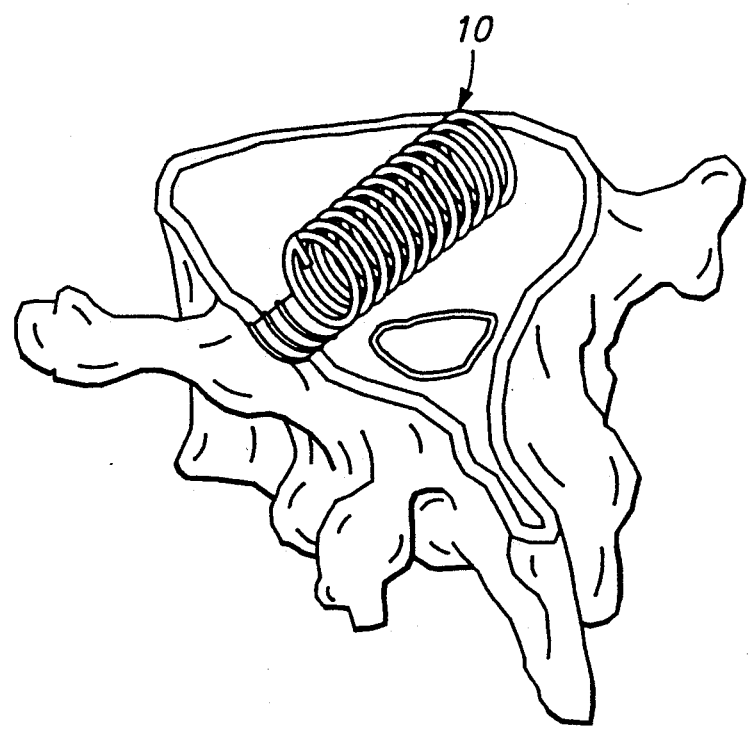
FIG. 9 is a view similar to FIG. 8, showing a single coil fusion implant.

FIG. 9 is a view similar to FIG. 8, showing a single coil 10 centered along the ventral body or centrum of a supporting vertebra. If the coil 10 were to be centrally aligned with the vertebral foramen, it would have to be inserted anteriorly. However, a single coil 10 can be inserted by using a posterolateral approach. This would position the coil at an angle across the center of the joint, as shown in FIG. 9. The implanted coil 10 should be located with its center coincident with the center of the joint to provide symmetry in the resulting implant. The exact angle of the implanted coil 10 will be dictated by the location at which access to the lamina is available in a particular surgical situation.

Figure 10:
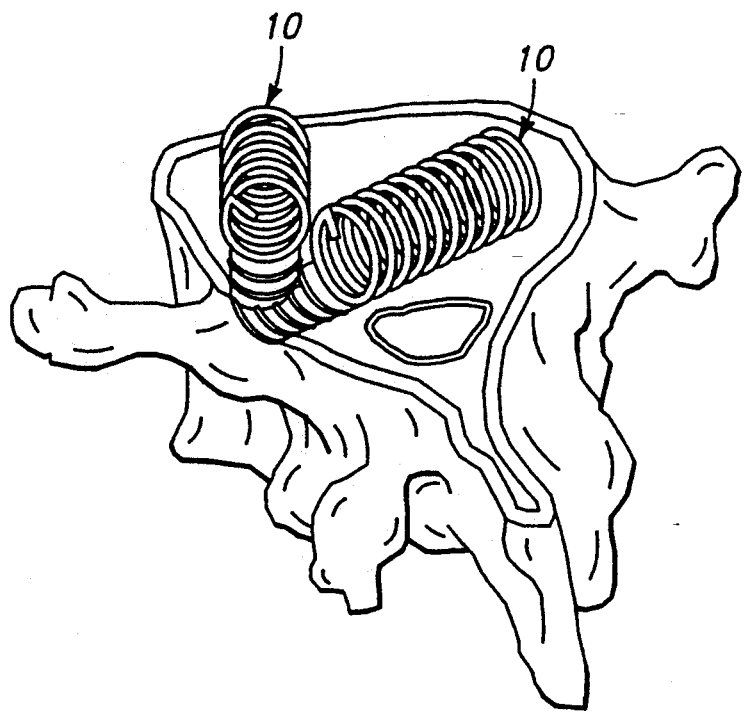
FIG. 10 is a view similar to FIG. 8, showing two coil fusion implants inserted from one side only.

FIG. 10 is a view of two implants inserted from one side only. They are of equal diameter but different length. The short one must be inserted first. If the approach is from the left side (as shown), then the longer implant must be centered to the right of the center of the disk for best fixation.

Figure 11:
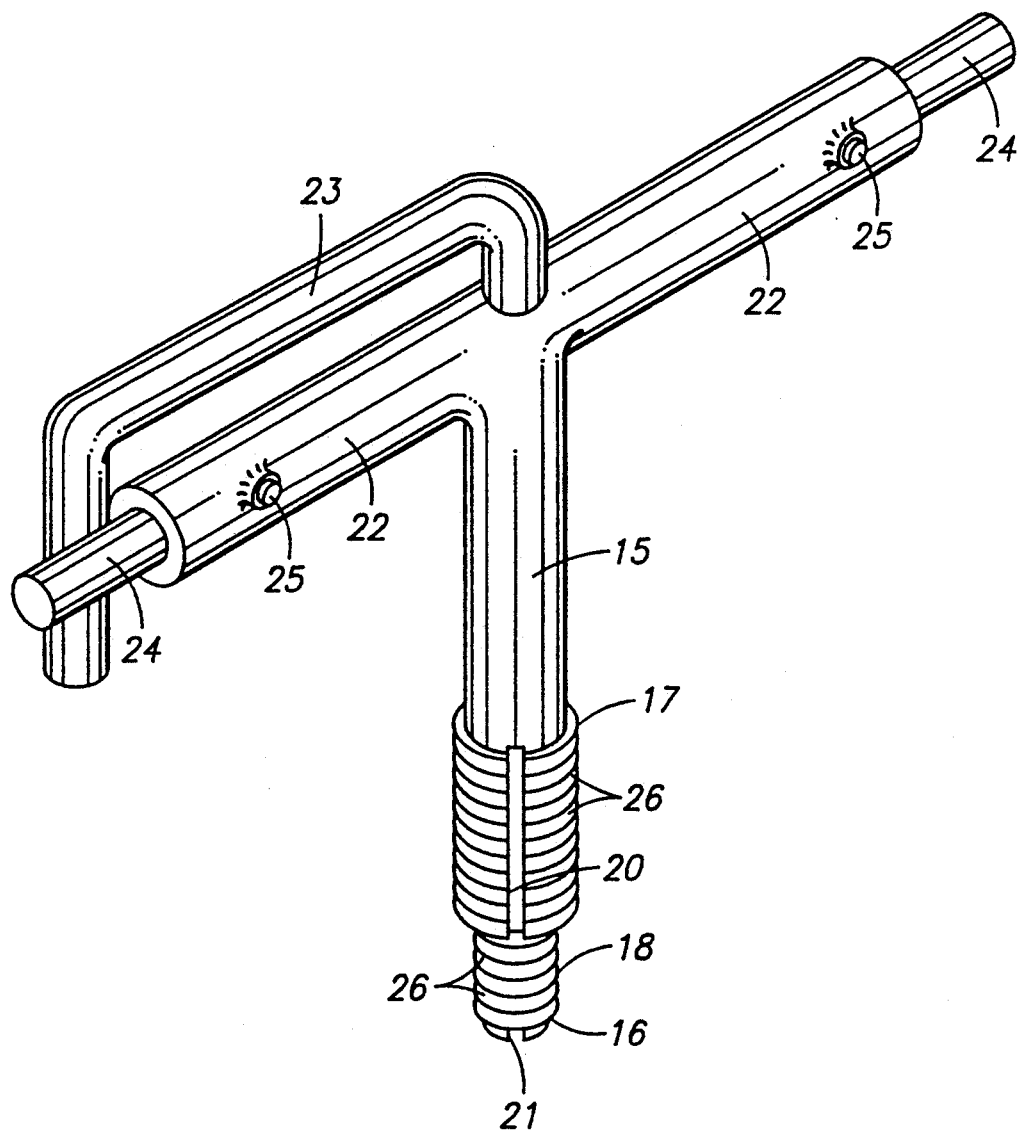
FIG. 11 is a perspective view of a prototype insertion tool for the implant.

FIG. 11 illustrates the general structure of a prototype manual insertion tool for the coil 10 shown in FIGS. 1-3. It has two specific functions. One is to torque or constrain the implant coil. The second is to act as an insertion tool similar to a self-retaining screw driver.

The tool comprises first and second coaxial members 15, 16. They partially overlap one another and are freely rotatable relative to each other about a common central axis. Both are illustrated as being cylindrical in shape, the first member 15 being tubular and the second member 16 being a solid rod.

The first member 15 has an outer surface 17 formed about the common central axis of the two coaxial members. It also has a coaxial inner surface. The outer and inner surfaces of the first member 15 are separated by the thickness of the tubular material from which the it is constructed.

The second member 16 has an outer surface 18 that extends axially outward from the adjacent axial end of the first member 15.

A first attachment means, shown as an axial groove or slot 20, is provided along the inner end of the first member 15 for releasably gripping the outer terminal section 13 of a coil 10. A second attachment means, in the form of a transverse radial groove or slot 21, is provided at the inner end of the second member 16 for releasably gripping the inner terminal section 12 of a coil 10.

The outer end of the first member 15 is provided with opposed crank handles 22 that serve as manual cranks for controlling the angular position of member 15 about its central axis. The outer end of the second member 16 includes a single manual crank arm 23 for controlling the angular position of member 16 about its coaxial central axis.

The radial end of crank arm 23, which protrudes outwardly from the first member 15, is bent back axially in a direction parallel to the surfaces 17 and 18. It intersects retractable stops 24 movably supported at the outer ends of handles 22. Each stop 24 is spring biased within the supporting handle 22. The stops 24 are normally maintained in an outwardly extended position as shown in FIG. 11.

Stops 24 can be selectively retracted by first releasing interior locks (not shown) controlled by depressible buttons 25 at the side of each handle 22. With a stop 24 retracted, the outer end of crank arm 23 is free to rotate past the respective radial end of a handle 22 to twist or recoil a coil fusion implant gripped by the two relatively rotatable members 15 and 16.

To assure accurate axial positioning of a coil 10 wound about outer surfaces 17 and 18 on the first and second relatively rotatable members 15 and 16, it is contemplated that the surfaces 17 and 18 will be provided with a helical pattern of grooves as shown in FIG. 11. As a coil 10 is tightened about the surfaces 17 and 18, the turns of the coil will seat in the grooves 26 to axially position them relative to one another. This will facilitate subsequent mating of the outer surfaces of coil 10 with threads formed in the receiving bony surfaces of the joint to be fused.

Insertion of a coil 10 between prepared bony surfaces of a joint, is generally illustrated in FIGS. 4–7. The process involves first selecting an appropriately sized coil 10 for the surgery being planned and then reducing the diameter of the coil by winding it tightly against the outer surfaces 17,18 of the relatively rotatable members 15,16 on the insertion tool. Winding of coil 10 can be accomplished manually, by manipulation of a tool such as that shown in FIG. 11, or by a more elaborate, motor driven or manually-controlled insertion tool. In either case, coil 10 will be reduced in diameter when in its torqued state and its inner surfaces will engage a supporting mandrel or other tool surface. The insertion tool must be capable of maintaining coil 10 in its torqued state as it is inserted between the bony surfaces of the joint being fused.

After initially inserting coil 10 between the prepared bony surfaces, preferably by threading it along prepared female threaded surfaces across the facing bones, the insertion tool holding the coil can be turned back and forth about its central axis to assure that the exterior surfaces of coil 10 are fully seated in the receiving bone. Coil 10 can also be pivoted back and forth a few degrees after it has been released to its expanded state to then allow it to seat even deeper into the supporting bony surfaces. This will assure that it expands as completely as possible in the implanted position.

After release of coil 10 and removal of the insertion tool, the implant cavity 11 within the coil and all remaining voids in the joint area are to be filled with bone chips or fragments. The bone graft materials should contact the living bone threads projecting radially inward through the implant cavity 11 between the recesses presented between the adjacent windings or turns of coil 10 to encourage bone growth into and through the recesses only at the disk space in the fused joint. Furthermore, bone growth should be encouraged about the outside of the coil(s) by roughening the facing bone surfaces adjacent to and just outside the implant. This will encourage bone fusion outside the coil(s) and discourage fibrosis or disk material invasion into the implant.

An attempt should be made to totally fill implant cavity 11 and to leave bone materials protruding both anterially and posterially from the implanted coil to encourage more avenues of fusion. In addition, bone material should protrude radially through the recesses and into the disk at that juncture. This should result in a bone graft across the space separating the bony surfaces and outside the ends of the implanted coil 10. Leaving the ends of coil 10 in an open condition or covering them with a non-metallic cap also makes possible visualization of the graft by X-ray techniques to determine the completeness and solid nature of the fusion process.

After insertion of coil 10, it should be allowed to recoil to its expanded state in a controlled manner. In the case of a tool as generally shown in FIG. 11, the coiled tension of the wound implant will maintain the outer end of crank arm 23 against one of the retractable stops 24 and the ends of handles 22. When it is desired to permit coil 10 to recoil, stops 24 can be manually retracted in a repetitive sequence while manually controlling relative rotational motion between handles 22 and crank arm 23 to allow the coil 10 to gradually recoil and enlarge radially. Manual release of stops 24 will progress back and forth between the two ends of handles 22 until coil 10 is fully expanded in opposition to the compressive forces exerted upon its individual windings by the engaged joint structure. At that point, the insertion tool can be retracted axially, allowing the outer and inner terminal sections 13 and 12 of coil 10 to release from the grooves or slots 20 and 21, respectively.

Should it ever be necessary to remove an implanted coil 10 from a joint after implantation surgery, an insertion tool, such as that shown in FIG. 11, can be moved axially inward through the expanded coil. After grippingly engaging its inner and outer terminal sections 12, 13, the coil 10 can be wound about the receiving surfaces of the insertion tool to reduce its outer diameter before unthreading it or pulling it from the implanted area.

The surgical system described above should make possible spinal fusion with much less surgery than other systems presently available. Assuming that a coil 10 can be sufficiently constrained when wound on an axial insertion tool, the insertion tool can also be passed through the surgical restriction available between adjacent vertebrae and released into a prepared bed without requiring any other tool access during insertion. The insertion tool, because of its reduced diameter, lends itself to possible percutaneous surgical procedures for spinal fusion purposes.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A method for stabilizing a human or animal joint, such as a spinal joint between adjacent vertebrae, formed by opposed bony surfaces covered and separated by intervening cartilage and surrounded by ligaments which resist expansion of the joint, and promoting bone growth across the stabilized joint, the method comprising the following steps:

surgically accessing the joint;

selecting a suitably sized fusion implant for placement between the opposed bony surfaces of the joint, the fusion implant including:
  (a) a coil formed as a length of wire that is spirally wound in repetitive turns centered about a common reference axis, the wire being constructed of elastic material capable of restoring the turns of the coil to radially expanded states after the coil has been twisted about the reference axis to a torqued state where the turns of the coil have reduced diameters;
  (b) the coil encircling an axial implant cavity adapted to receive material promoting bone ingrowth through the implant;
  (c) the wire including first and second terminal sections at opposite ends of the coil adapted to facilitate gripping of the wire and relative twisting of the ends of the coil about the reference axis;
  (d) the coil having sufficient compressive strength and elasticity to maintain separation between bony surfaces of a prepared joint when implanted and permitted to assume a conforming expanded state;
  (e) the implanted coil being adapted to have no interconnections attached to its turns that would interfere with projection of prepared bone surfaces radially inward into its axial implant cavity;

gripping the first and second terminal sections;

twisting the coil in the direction in which the wire is wound about the reference axis to a reduced diameter torqued state in which the outer diameter of the coil is less than its outer diameter while in its relaxed state;

introducing the twisted coil between the opposed bony surfaces of the joint; and releasing one or both terminal sections of the coil to allow the coil to assume an expanded state, whereby the outer diameter of the coil is radially enlarged relative to its torqued state and the joint is immediately stabilized by spreading the bony surfaces apart in opposition to the resistance to expansion of the joint provided by the surrounding ligaments.

2. The method of claim 1, including the following step after the releasing step:
  filling the coil and remaining voids in the surrounding joint area with material promoting bone ingrowth through the implant.

3. The method of claim 1, wherein the twisted coil is threadably introduced between the opposed bony surfaces of the joint.

4. The method of claim 1, including the following step prior to the step of introducing the coil:
  removing intervening cartilage located between the opposed bony surfaces of the joint in the vicinity immediately adjacent and exterior to the intended placement of the coil implant.

5. The method of claim 1, including the following steps prior to the step of introducing the coil:
  removing intervening cartilage located between the opposed bony surfaces of the joint in the vicinity immediately adjacent and exterior to the intended placement of the coil implant; and
  boring a cylindrical opening across the opposed bony surfaces.

6. The method of claim 1, including the following steps prior to the step of introducing the coil:
  removing intervening cartilage located between the opposed bony surfaces of the joint;
  boring a cylindrical opening across the opposed bony surfaces; and
  forming female threads along the cylindrical opening, the depth and spacing of the threads being complementary to the radial thickness and axial spacing of the adjacent turns of the coil while in its expanded state.

7. The method of claim 1, including the following steps prior to the step of introducing the coil:
  spreading the bony surfaces apart in opposition to the surrounding ligaments;
  forming a threaded bore between the surfaces; and
  allowing the bony surfaces to move toward one another while continuing thread formation.

8. The method of claim 1, including the following steps prior to the step of introducing the coil:
  spreading the bony surfaces apart in opposition to the surrounding ligaments;
  forming a threaded bore between the surfaces; and
  forcing the bony surfaces toward one another while continuing thread formation.

* * * * *